(12) United States Patent
Cisko et al.

(10) Patent No.: US 11,679,016 B2
(45) Date of Patent: Jun. 20, 2023

(54) HERNIA BELT

(71) Applicant: Hollister Incorporated, Libertyville, IL (US)

(72) Inventors: George J. Cisko, Spring Grove, IL (US); Christina Augustyn, Chicago, IL (US); Ryan S. Park, Northbrook, IL (US); Donald Rakevicius, Lake Zurich, IL (US); Xuemei Wang, Buffalo Grove, IL (US); Stephanie Kia, Columbus, OH (US); Jeffrey R. Burger, Bexley, OH (US)

(73) Assignee: Hollister Incorporated, Libertyville, IL (US)

( * ) Notice: Subject to any disclaimer, the term of this patent is extended or adjusted under 35 U.S.C. 154(b) by 987 days.

(21) Appl. No.: 16/478,639

(22) PCT Filed: Jan. 30, 2018

(86) PCT No.: PCT/US2018/015955
§ 371 (c)(1),
(2) Date: Jul. 17, 2019

(87) PCT Pub. No.: WO2018/144456
PCT Pub. Date: Aug. 9, 2018

(65) Prior Publication Data
US 2020/0046540 A1    Feb. 13, 2020

Related U.S. Application Data

(60) Provisional application No. 62/453,155, filed on Feb. 1, 2017, provisional application No. 62/551,370, filed on Aug. 29, 2017.

(51) Int. Cl.
*A61F 5/24* (2006.01)
*A61F 5/03* (2006.01)
(Continued)

(52) U.S. Cl.
CPC .............. *A61F 5/24* (2013.01); *A61F 5/02* (2013.01); *A61F 5/03* (2013.01); *A61F 5/30* (2013.01); *A61F 5/449* (2013.01)

(58) Field of Classification Search
CPC .... A61F 5/02; A61F 5/028; A61F 5/03; A61F 5/24; A61F 5/28; A61F 5/30; A61F 5/449;
(Continued)

(56) References Cited

U.S. PATENT DOCUMENTS 2,185,834 A     1/1940 Creper
9,579,237 B2 *  2/2017 Hansen ................. A61F 13/148
(Continued)

FOREIGN PATENT DOCUMENTS

CN    204016581 U    12/2014
TW    M534601 U  *  1/2017  ............... A61F 5/37

OTHER PUBLICATIONS

International Preliminary Report on Patentability and Written Opinion issued by International Bureau in connection with PCT/US2018/015955 dated Aug. 15, 2019.

*Primary Examiner* — Keri J Nelson
(74) *Attorney, Agent, or Firm* — Levenfeld Pearlstein, LLC

(57) ABSTRACT

A hernia belt (500) may include a digitally knitted support belt (502) and a two-part fastening system (504,505). The two-part fastening system may include a first part (504) and a second part (505), in which the second part includes a plurality of fastener strips (508, 510, 512, 514, 516) arranged spaced apart from each other. The digitally knitted support belt may include mesh stitch layouts (518, 520, 522) for providing breathability and support.

3 Claims, 16 Drawing Sheets

(51) Int. Cl.
*A61F 5/30* (2006.01)
*A61F 5/449* (2006.01)
*A61F 5/02* (2006.01)

(58) Field of Classification Search
CPC .. A61F 13/0273; A61F 13/062; A61F 13/085; A61F 13/102; A61F 13/108; A61F 13/14; A61F 13/148; A61F 2013/00102; A61F 2013/00127
See application file for complete search history.

(56) References Cited

U.S. PATENT DOCUMENTS

2006/0047256 A1  3/2006  Levesque
2009/0171259 A1  7/2009  Soerensen et al.

* cited by examiner

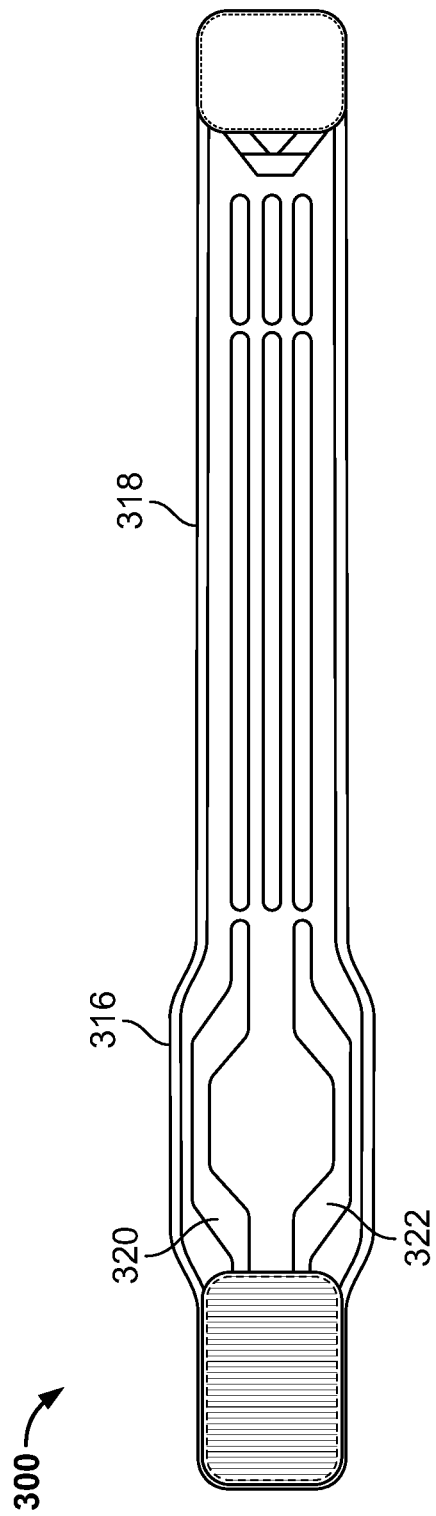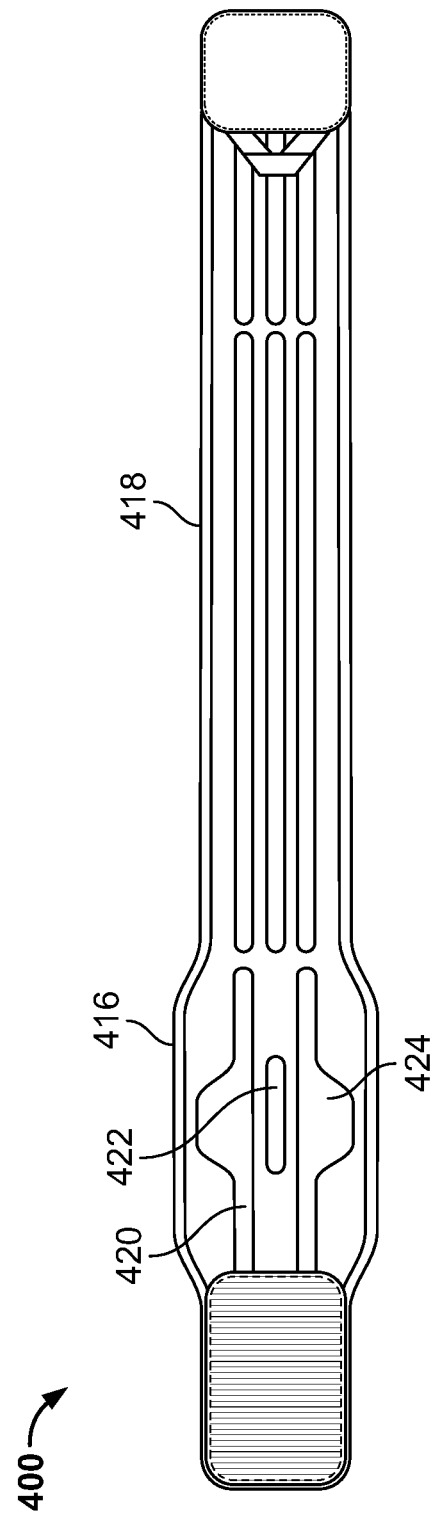

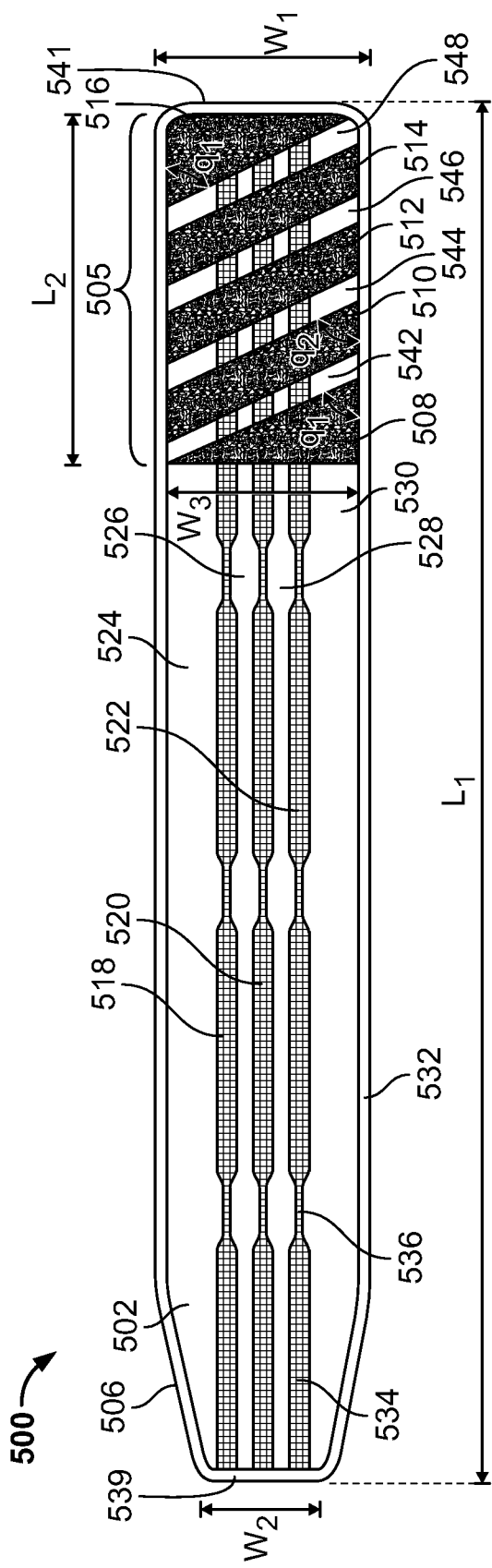
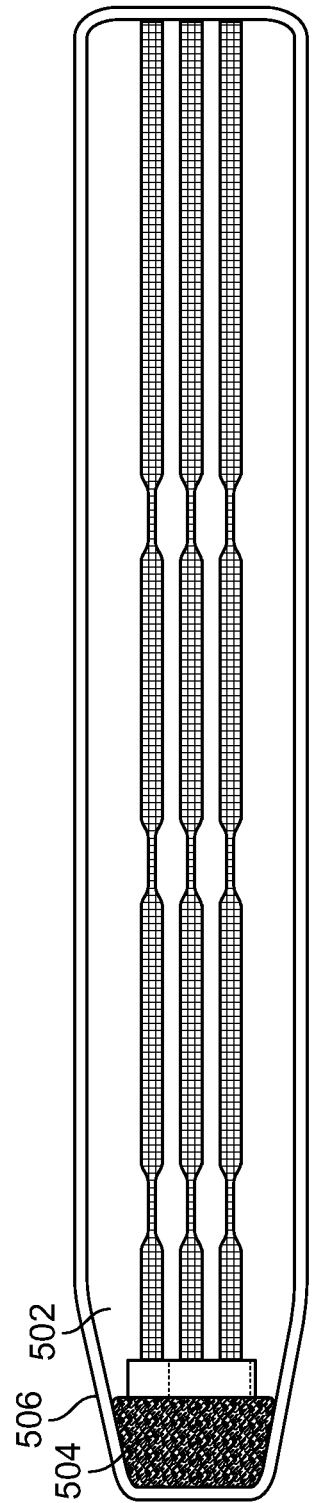
FIG. 10A
FIG. 10B

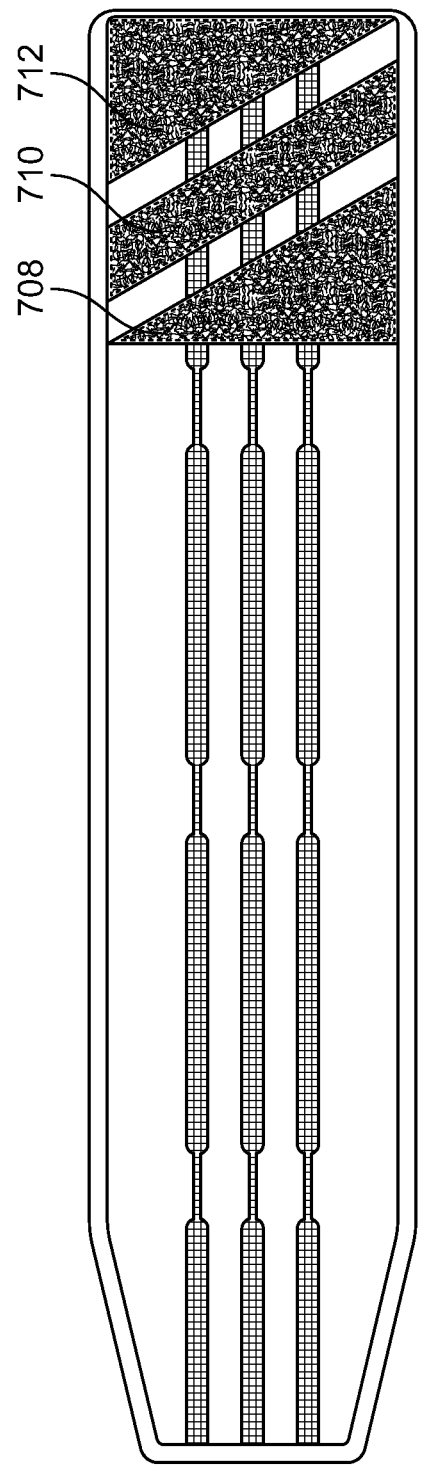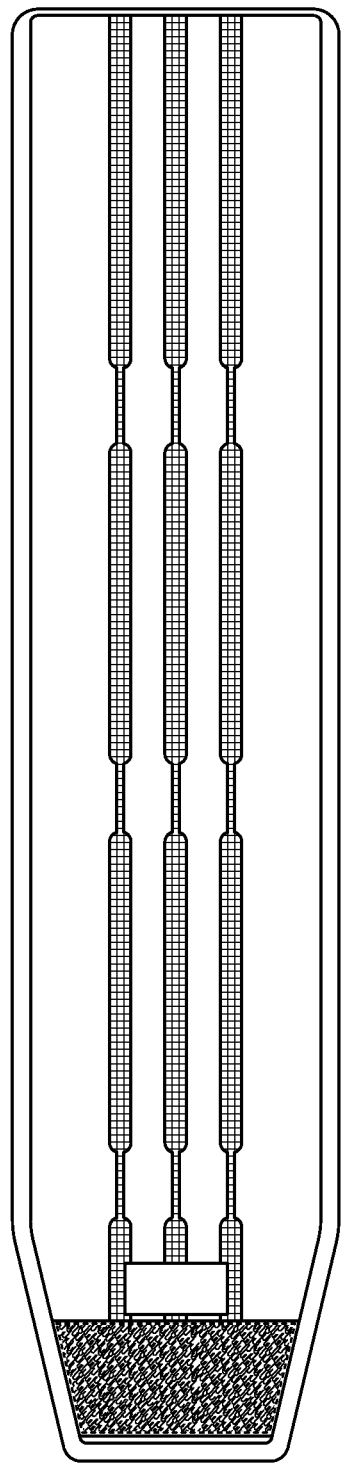
FIG. 15A
FIG. 15B

HERNIA BELT

This is a National Stage Application of International Patent Application No. PCT/US2018/015955, filed Jan. 30, 2018, which claims the benefit of and priority to U.S. Provisional Application No. 62/453,155, filed Feb. 1, 2017 and U.S. Provisional Application No. 62/551,370, filed Aug. 29, 2017, the entirety of which are incorporated fully herein by reference.

BACKGROUND

The present disclosure generally relates to an abdominal support device, and in particular, a support belt to aid in the prevention of a hernia and management of a herniated stoma.

A hernia is a rip or a tear in the muscle tissue of an abdomen which causes the abdominal contents, such as a portion of intestine, to bulge out. The hernia may cause pain and discomfort. Ostomates have an increased risk of hernia from having a stoma. A stoma is formed on an abdomen surface by passing through the abdominal wall, thus creating a potential site of weakness. Further, the abdominal wall muscles that fit around a stoma may come away from the edges of the stoma, causing a parastomal hernia.

A parastomal hernia can be very uncomfortable and can cause difficulties in managing and caring for the stoma. It is also more difficult to securely attach an ostomy bag around a herniated stoma. It can also lead to intestinal twisting or kinking that can cause serious damage by cutting off blood vessels.

Various products have been introduced to support the abdomen, such as an abdominal compression garment disclosed in Soerensen et al., US Patent Application Publication No. 2009/0171259, and an ostomy belt disclosed in Levesque, US Patent Application No. 2006/0047256. The present disclosure provides a hernia belt for providing improved abdominal support and comfort for wearers.

BRIEF SUMMARY

In one aspect, a hernia belt comprising a support belt formed from a stretchable material and a two-part fastening system is provided. The two-part fastening system is configured to secure the hernia belt on a user's body and may include a first part arranged on the support belt proximate a first peripheral end and a second part comprising a plurality of fasteners arranged spaced apart from each other on the support belt proximate a second peripheral end. The spaced arrangement of the fasteners may provide an extended fastener area while still allowing the underlying support belt to stretch between fasteners.

The first part may comprise a single fastener strip attached to a back side surface of the support belt. The second part comprising the plurality of fasteners may be attached to a front side surface of the support belt, in which each of the plurality of fasteners is separated from each other with a gap therebetween.

In an embodiment, the plurality of fasteners may include a first fastener strip, a second fastener strip, a third fastener strip, a fourth fastener strip, and a fifth fastener strip, wherein the second, third, fourth fastener strips are arranged between the first and fifth fastener strips with the fifth fastener strip arranged proximate the second peripheral end of the support belt. Each of the first and fifth fastener strips may have a generally triangular shaped body, while each of the second, third, and fourth fastener strips may have a generally parallelogram shaped body. In such an embodiment the plurality of fasteners may be arranged diagonally, wherein the first fastener strip is arranged adjacent the second fastener strip with a gap therebetween, and the third fastener strip is arranged adjacent the second fastener strip with a gap therebetween, and the fourth fastener strip is arranged adjacent the third fastener strip with a gap therebetween, and the fifth fastener strip is arranged adjacent the fourth fastener strip with a gap therebetween.

In another embodiment, the plurality of fasteners may be arranged vertically, wherein each of the plurality of fasteners may have a generally rectangular body and arranged spaced apart from an adjacent fastener with a gap therebetween.

The support belt may be formed from a one-piece knit construction and may comprise background areas, mesh layouts, and boundary areas, wherein the mesh layouts are configured to provide larger gaps between stitches than the background areas when stretched to provide breathable areas. The support belt may be configured to have a generally rectangular shaped body including a tapered portion proximate the first peripheral end. Further, the support belt may be provided with rounded corners for user comfort. In another embodiment, the support belt may comprise more than a one-piece knit construction. For example, the support belt may be formed from two-piece knit constructions, which may be stitched together to form the support belt.

In another aspect, a hernia belt comprising a support belt formed from a one-piece knit construction and a two-part fastening system configured to secure the hernia belt on the user's body is provided. The support belt may comprise background areas, mesh layouts, and boundary areas framing the shape of the support belt. The mesh layouts may be configured to provide larger gaps between stitches than the background areas when stretched to provide breathable areas. The mesh layouts may comprise double jersey stitches and exposed inlay spandex yarns knitted between double jersey layers.

The support belt may be digitally knitted to provide the one-piece knit construction. The mesh layouts may be knitted using four ends polyamide yarns including two front and two back, two ends spandex yarns including one front and one back, and an alternating inlay spandex yarn, wherein at least some portions of the alternating inlay spandex yarn may be exposed and visible from the front side of the support belt. The background areas may comprise double jersey stitches and an embedded inlay. The background areas may be knitted using four ends polyamide yarns including two front and two back, two ends spandex yarns including one front and one back, and an embedded inlay spandex yarn.

The boundary areas my include an upper boundary area, a lower boundary area, and side boundary areas. The upper boundary area may comprise an outer cast-on stitch layout knitted using four ends polyamide yarns and two ends spandex yarns, and an inner mesh layout. The lower boundary area may comprise an outer bind-off stitch layout knitted using four ends polyamide yarns including two front and two back, and an inner mesh layout. The mesh layouts may be knitted using four ends polyamide yarns including two front and two back, two ends spandex yarns including one front and one back, and an alternating inlay spandex yarn, wherein at least some portions of the alternating inlay spandex yarn may be exposed and visible from a front side of the support belt. The side boundary areas may be knitted using a birdseye jersey roll self edge knitting operation to provide a curl around side edges and to conceal inlay looping.

The two-part fastening system may include a first part arranged on the support belt proximate a first peripheral end and a second part comprising a plurality of fasteners arranged spaced apart from each other on the support belt proximate the second peripheral end. The first part may comprise a single fastener strip attached to a back side surface of the support belt, while the plurality of fasteners are attached to a front side surface of the support belt, wherein each of the plurality of fasteners may be separated from each other with a gap therebetween.

The hernia belt according to any of the foregoing embodiments may be configured to have a force to stretch of about 0.2 kg per inch of a belt width per each 10% stretch of a belt length.

In yet another aspect, a hernia belt comprising a support belt including a wider front torso portion and a narrower portion, and a two-part fastening system is provided. The wider front torso portion may include a pattern for providing a visual cue for positioning the wider front torso portion over a target area. The support belt may be configured to wrap around a user's abdomen and back, while the two-part fastening system may be configured to secure the hernia belt accordingly on the user's body.

In an embodiment, the wider front torso portion may include a plurality of mesh stitch layouts defining the pattern. The plurality of mesh stitch layouts may be configured to provide a mesh-like structure when the hernia belt is stretched to provide air flow paths. The plurality of mesh stitch layouts may include an upper mesh layout, a center mesh layout, and a lower mesh layout. The center mesh layout may extend across the wider front torso portion about the center of the width of the wider front torso portion. The upper and lower mesh layouts may extend generally parallel to the center mesh layout in a front section, and slope away from the center mesh layout and further extend generally parallel to the center mesh layout at an increased distance apart in a center section. The upper and lower mesh layouts may taper back toward the center mesh layout and extend generally parallel to the center mesh layout in a back section.

The narrower portion may also include at least one mesh stitch layout configured to provide a breathable area. In an embodiment, the narrower portion may include three mesh stich layouts extending generally parallel to each other.

In some embodiments, the support belt may be knitted via a digital knit technology incorporating a plurality of stitch types using polyamide yarns and spandex yarns. The support belt may include a background stitch area, a plurality of mesh stitch layouts surrounded by the background stitch area, and boundary stitch areas framing the shape of the support belt. The background stitch area and the plurality of mesh stitch layouts may comprise horizontal inlays knitted using spandex yarns to provide sufficient compressive support to a hernia. Further, the boundary stitch areas may be knitted using polyamide yarns and spandex yarns, and may be configured to prevent curling of the hernia belt. The support belt may be configured such that the plurality of mesh stitch layouts has larger gaps between stitches than the background stitch area when stretched to provide breathable areas.

The two-part fastening system may include a first fastener and a second fastener. The first fastener may be attached to a first peripheral end of the support belt, while the second fastener is attached to a second peripheral end of the support belt, such that the first and second fasteners may engage each other to secure the hernia belt on a user.

In another aspect, a hernia belt comprising a support belt knitted using a digital knit technology incorporating a plurality of stitch types is provided. The support belt may include a background stitch area, a plurality of mesh stitch layouts surrounded by the background stitch area, and boundary stitch areas framing the shape of the support belt. The support belt may include a wider front torso portion and a narrower portion. The wider front torso portion may include a pattern defined by the plurality of mesh stitch layouts configured to provide a visual cue for positioning the wider front torso portion over a target area. The hernia belt may also include a two-part fastening system configured to secure the hernia belt on a user.

The plurality of mesh stitch layouts may be knitted to provide larger gaps between stitches than the background stitch area when stretched to provide breathable areas. Further, the background stitch area and the plurality of mesh stitch layouts may comprise horizontal inlays knitted using spandex yarns to provide sufficient compressive support to a hernia. In some embodiments, the support belt may be knitted using polyamide yarns and spandex yarns.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein:

FIG. 8 is a perspective view of a hernia belt including a wider front torso portion and a narrower portion according to an embodiment;

FIG. 9 is a perspective view of a hernia belt including a wider front torso portion and a narrower portion according to yet another embodiment;

FIGS. 10A-B are perspective front and back views of a hernia belt according to an embodiment;

FIG. 15A-B are perspective front and back views of a hernia belt according to another embodiment.

DETAILED DESCRIPTION

Figure 1:
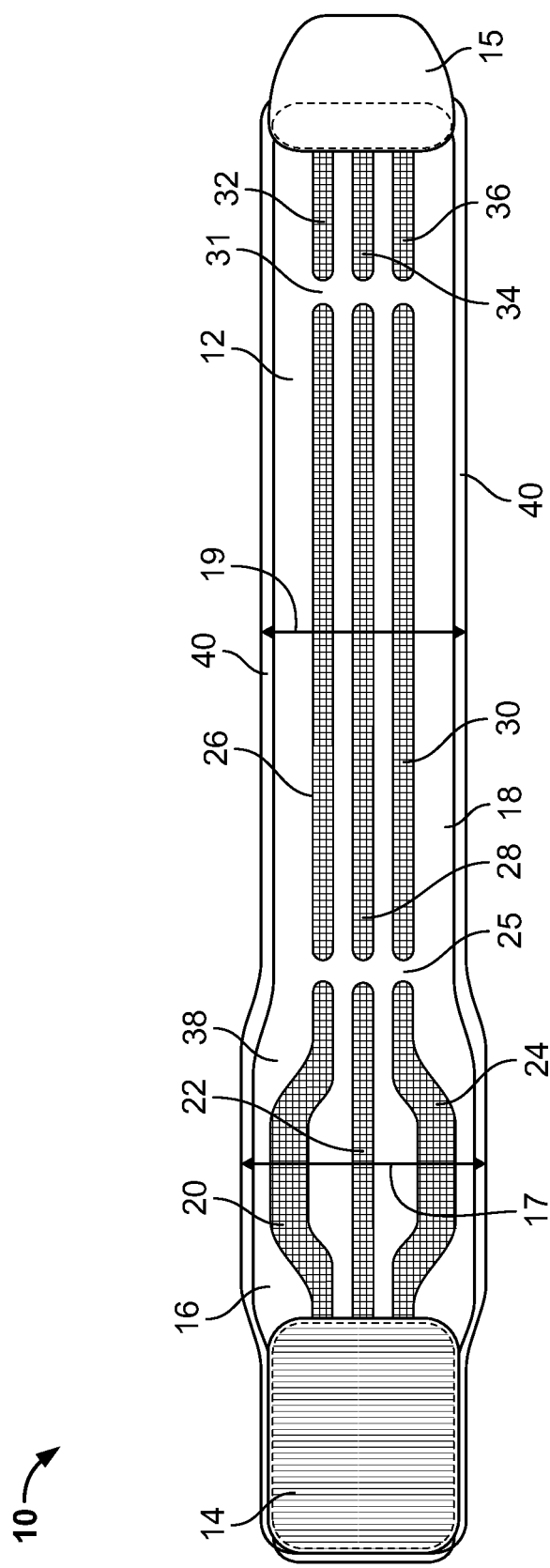
FIG. 1 is a perspective view of a hernia belt including a wider front torso portion and a narrower portion according to an embodiment.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated. The words "a" or "an" are to be taken to include both the singular and the plural. Conversely, any reference to plural items shall, where appropriate, include the singular.

Referring now to the figures, FIG. 1 shows a hernia belt 10 according to an embodiment. The hernia belt 10 may generally include a support belt 12 formed from a stretchable knitted material and a two-part fastening system 14, 15. The support belt 12 may be formed as a one-piece knit construction via a knitting process. In this embodiment, the support belt 12 may include a wider front torso portion 16 and a narrower portion 18. The wider front torso portion 16 may be configured to provide support for a peristomal area over an ostomy appliance. The wider front torso portion 16 may have a maximum width 17, which is greater than a width 19 of the narrower portion 18.

The support belt 12 may be knitted using a number of different yarns incorporating a plurality of stitch types. The support belt 12 may be configured to stretch about 10% to about 40%.

Figure 2:
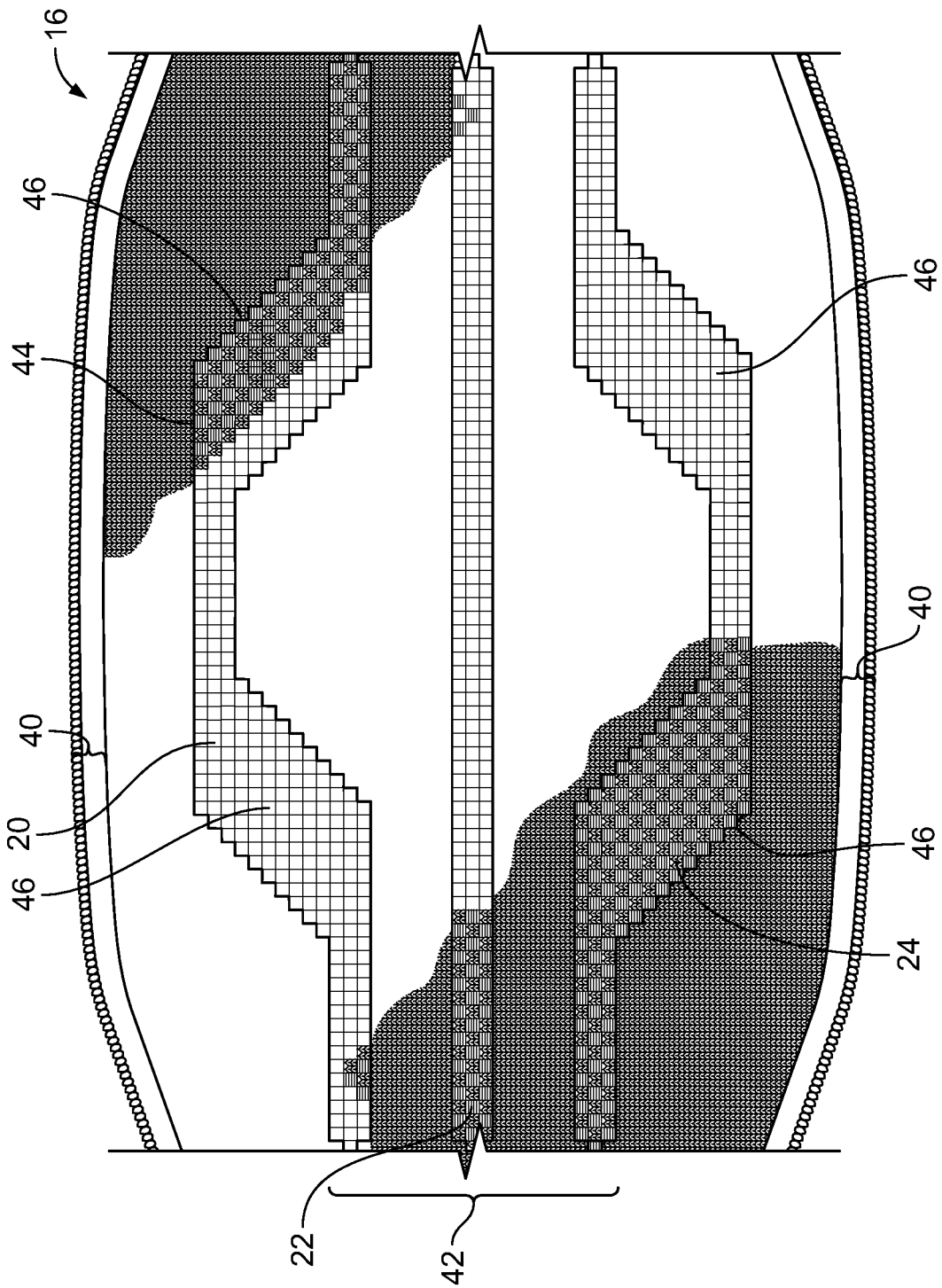
FIG. 2 is an enlarged view of the wider front torso portion of the hernia belt of FIG. 1.

In an embodiment, the support belt 12 may comprise a plurality of mesh stitch layouts 20, 22, 24, 26, 28, 30, 32, 34, 36, background stitch areas 38, and boundary stitch areas 40. The mesh stitch layouts 20, 22, 24, 26, 28, 30, 32, 34, 36 may be configured to provide breathable areas to allow airflow through the hernia belt 10 to user's skin. In such an embodiment, the mesh stitch layouts may be configured to stretch to a mesh-like structure providing air path when the hernia belt 10 is stretched and worn. Further, the mesh stitch layouts may be configured to provide sufficient compression to support a herniated peristomal area while proving breathability. For example, the mesh stitch layouts may be formed using a combination of stretchy yarns, such as spandex yarns, and stiff yarns, and may comprise horizontal knit inlays and/or weave-ins to provide compression along the abdomen to prevent a hernia or to support a herniated peristomal area. In some embodiments, the mesh stitch layouts may have a mesh-like pattern design including darker portions that look like holes as shown in FIGS. 1 and 2 to make the mesh stitch layouts stand out and provide visual reading of the breathable areas.

The mesh stitch layouts 20, 22, 24, 26, 28, 30, 32, 34, 36 may be surrounded by the background stitch areas 38. The background stitch area 38 may be configured to provide sufficient compression to prevent a hernia or to support a herniated peristomal area. In an embodiment, the background stitch areas 38 may be formed using a combination of soft polyamide yarns, such as nylon 66 yarns, and stretchy yarns, such as spandex yarns, to provide an adequate knit tension for the required compression while providing desirable softness against skin and capability to wick sweat and moisture for improved user comfort.

The outer perimeters of the support belt 12 may be provided with the boundary stitch areas 40. The boundary stitch areas 40 may be configured to frame the shape of the support belt 12 including the wider front torso portion 16 and the narrower portion 18. Further, the boundary stitch area 40 may be configured to prevent curling of the hernia belt 10 while wearing and moving. In an embodiment, the boundary stitch areas 40 may comprise spandex yarns to reduce curling of the hernia belt 10.

The wider front torso portion 16 may comprise an upper mesh layout 20, a center mesh layout 22, and a lower mesh layout 24. The upper and lower mesh layouts 20, 24 may be configured to provide a visual cue for a user to position the hernia belt 10 to generally center the wider front torso portion 16 over the stoma. Further, the upper and lower mesh layouts 20, 24 may have a geometrical shape to maximize flexibility and airflow while applying sufficient compression proximate the peristomal area.

In the embodiment of FIG. 2, the upper, center, and lower mesh layouts 20, 22, 24 may extend generally parallel to each other with the center mesh layout 22 extending generally in the center of the width of the wider front torso portion 16. As the width of the wider front torso portion 16 gradually increases, the upper and lower mesh layouts 20, 24 may slope away from the center mash layout 22, such that a distance between the upper and lower mesh layouts 20, 24 increases from a front section 42 to a center section 44 of the wider front torso portion 16. The upper and lower mesh layouts 20, 24 may extend cross the center section 44 of the wider front torso portion at an increased distance apart, and taper back towards the center mash layout 22 as the wider front torso portion 16 transitions to the narrower portion 18. In some embodiments, sloped sections 46 may include a greater number of stitches to provide larger mesh layout areas when compared to other sections of the mesh layouts to maximize flexibility and breathability around the peristomal area while providing sufficient compression to support a herniated peristomal area.

The narrower portion 18 may comprise three mesh layouts 26, 28, 30, which are configured to provide flexibility and breathability along the user's back while providing sufficient compression in specific areas of the abdomen to help support a hernia. The center mesh layout 28 may extend horizontally across the center of narrower portion 18. The upper and lower mesh layouts 26, 30 may also extend horizontally and generally parallel to the center mesh layout 28. As shown in FIG. 1, the mesh layouts 26, 28, 30 may extend even with the mesh layouts 20, 22, 24 of the wider front torso portion 16 with a gap 25 therebetween proximate a transition between the wider front torso portion 16 and the narrower portion 18. In some embodiments, the mesh layouts 26, 28, 30 may extend across only a portion of the narrower portion 18. For example, in the embodiment of FIG. 1, the narrower portion 18 may include the mesh layouts 20, 22, 24, which extend a substantial portion of the narrower portion 18, and mesh layouts 32, 34, 36, which extend following the mesh layouts 26, 28, 30 with a gap 31 therebetween.

The two-part fastening system comprising first and second fasteners 14, 15 for securing the hernia belt 10 around a user's abdomen may be attached to each peripheral end of the support belt 12. In an embodiment, the two-part fastening system may comprise hook and loop fasteners as marketed under the Velcro trademark. Alternatively, the first and second fasteners 14, 15 may comprise a polypropylene material of the type sold under the trademark DUOTEC by G. Binder GmbH & Co. Holzgerlingen, Germany, which is stated in product literature to work on the principle of interlocking mushroom elements, which are designed so both fasteners can be identical. Each of the first and second fasteners 14, 15 may be configured to include tapered and curved edges as shown in FIG. 1 to provide comfort to a user when sitting and moving.

Figure 3:
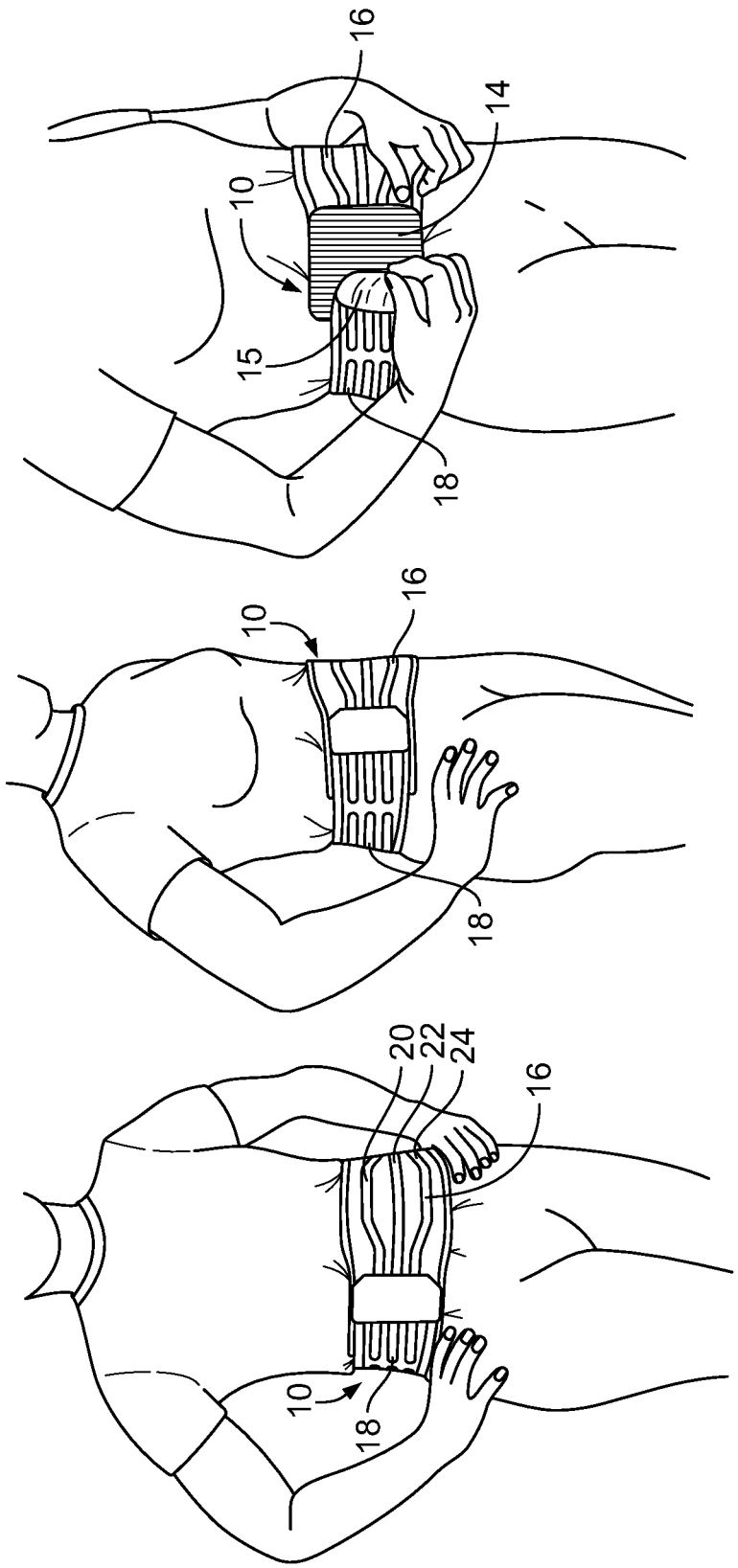
FIGS. 3A-C are illustrations of a user wearing the hernia belt of FIG. 1.

FIGS. 3A-C are illustrations of a user wearing the hernia belt 10. As shown, the hernia belt 10 includes a wider front torso portion 16 providing support to a stoma by applying compression pressure over the stoma. The wider front torso portion 16 includes mesh layouts 20, 22, 24 providing a visual cue for positioning the wider front torso portion 16 over the stoma while providing breathability and support for a herniated peristomal area. The hernia belt 10 is secured in place by wrapping the narrower portion 18 around the user's abdomen and engaging the two-part fastening system 14, 15.

Figure 4:
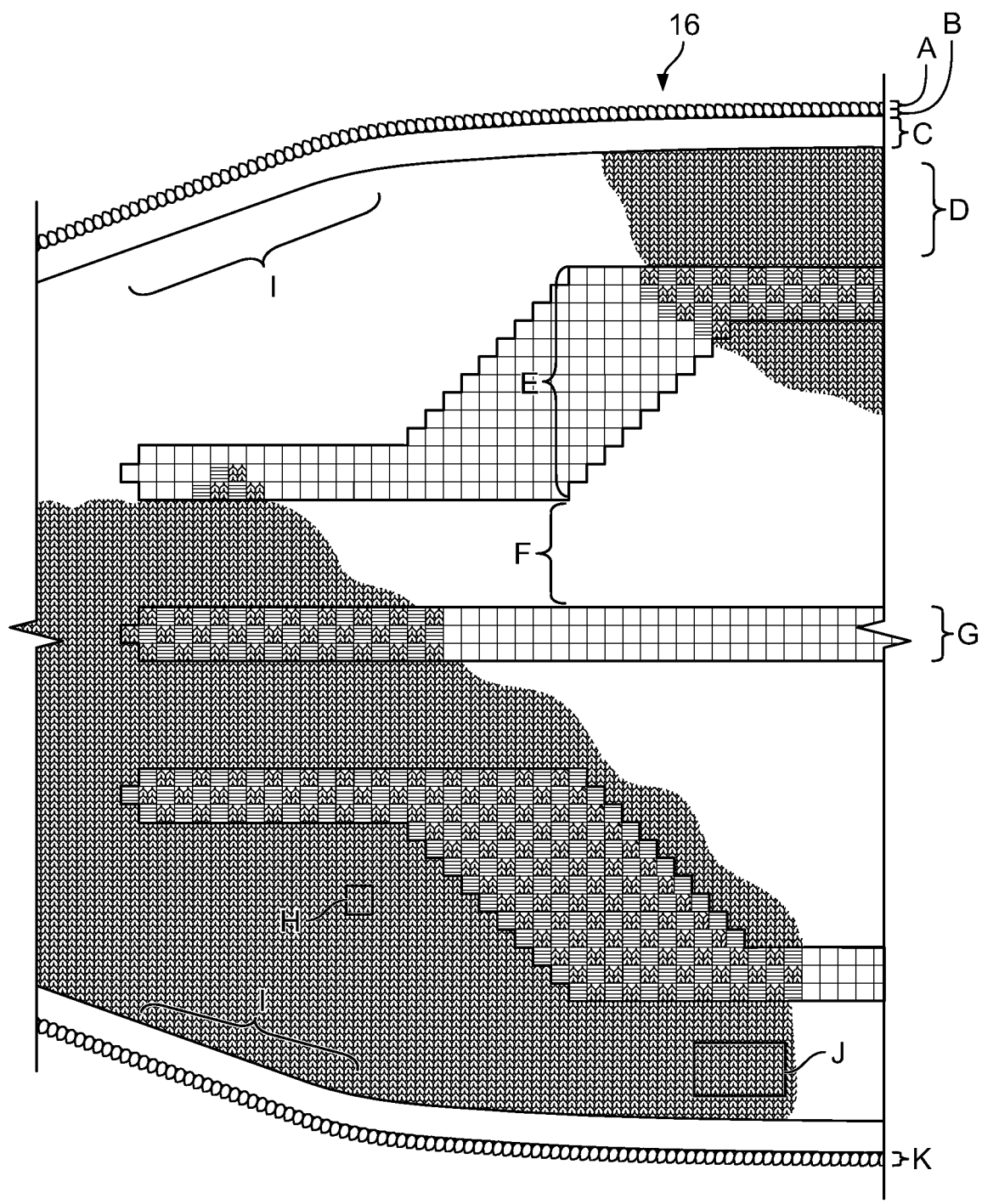
FIG. 4 is an enlarged view of a wider front torso portion of a hernia belt according to an embodiment.

In an embodiment, the support belt 12 may be made via digital knit technology. Referring to FIG. 4, an exemplary stitch/yarn layout for the wider front torso portion 16 according to an embodiment is provided.

Figure 5:
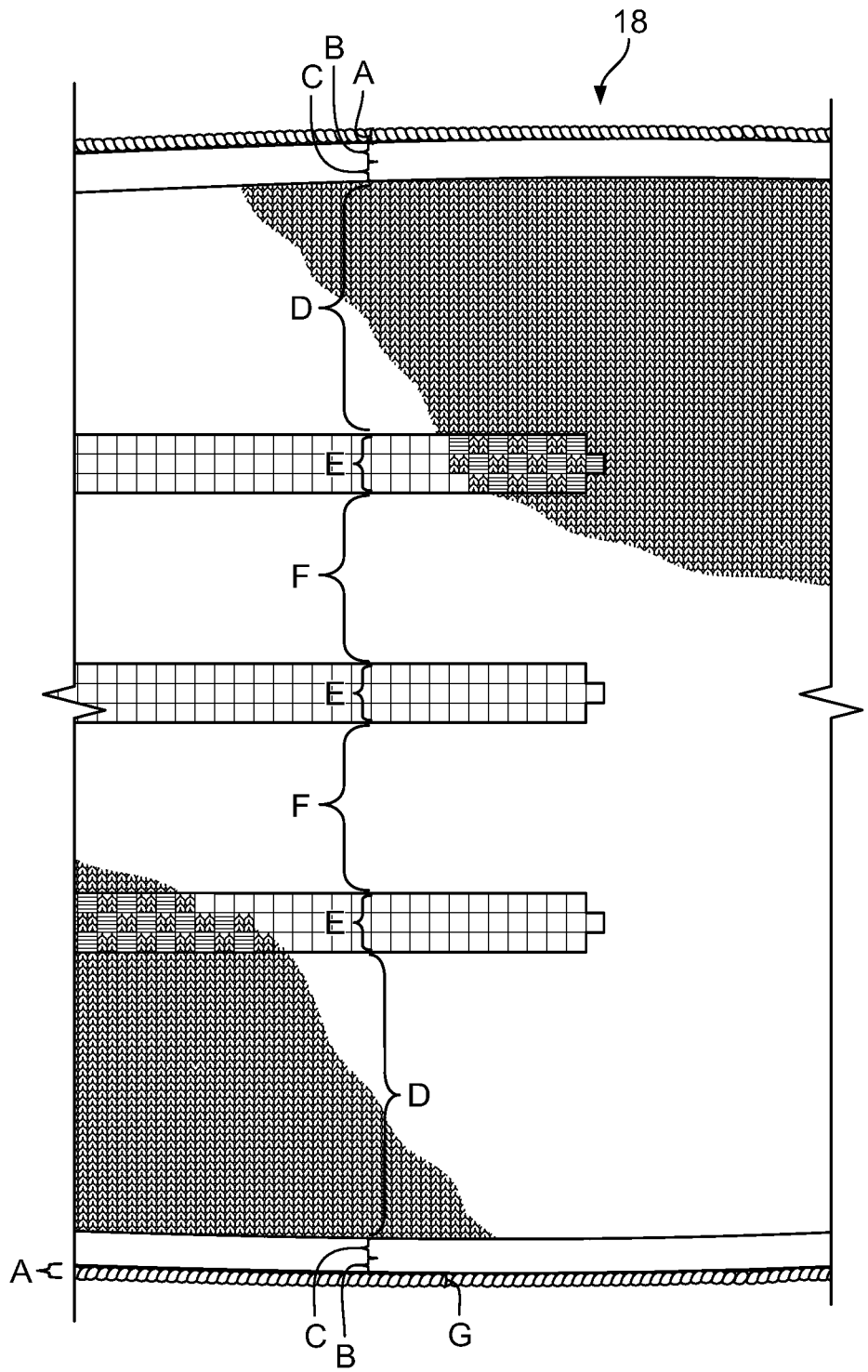
FIG. 5 is an enlarged view of the narrower portion of a hernia belt according to an embodiment.

A. Stitch: 1 Needle Cast-On Start
   Yarn: 2 Ends Polyamide+1 End Spandex
B. Stitch: 3 rows Double Jersey
   Yarn: 2 Ends Polyamide+1 End Spandex
C. Stitch: 4 rows Double Jersey Stitches+4 rows HORIZONTAL Inlay elastic sandwiched between Double Jersey layers
   Yarn: 4 Ends Polyamide+2 Ends Spandex+1 End Inlay Spandex
D. Stitch: 10-14 rows Double Jersey Stitches+HORIZONTAL Inlay Spandex yarn sandwiched between Double Jersey layers
   Yarn: 4 Ends Polyamide+2 Ends Spandex+1 End Inlay Spandex
E. Pattern Repeat Stitch: 14 rows: Float HORIZONTAL Inlay Spandex 2 needles to the FRONT exterior layer+alternating 2 needles Light Grey Double Jersey yarn coming to the FRONT. Inlay yarn is sandwiched between front and back double jersey layers in a HORIZONTAL direction.
   Yarn: 4 Ends Polyamide (2 front+2 back)+2 Ends Spandex (1 front+1 back)+1End Alternating Inlay Spandex
F. Stitch: 8-12 rows Double Jersey Stitches+HORIZONTAL Inlay Spandex yarn sandwiched between Double Jersey layers.
   Yarn: 4 Ends Polyamide+2 Ends Spandex+1 End Inlay Spandex
G. Stitch: Repeat=6 rows of 2 needles front floating Horizontal Spandex Inlay stitches+alternating 2 needle front Double Jersey polyamide yarn.
   Yarn: 4 Ends Polyamide (2 front+2 back)+2 Ends Spandex (1 front+1 back)+1End Alternating Inlay Spandex
H. Stitch: 2 needles Light Grey front Double Jersey boarder around "Faux Mesh" Pattern repeat.
I. Stitch: 6 Fully Fashioning Shaping Marks.
J. Stitch: Marl every other row.
K. Stitch: 1 needle Crochet finishing chain stitch Bind-Off Referring to FIG. 5, an exemplary stitch/yarn layout for the narrower portion 18 according to an embodiment is provided.

Figure 6A:
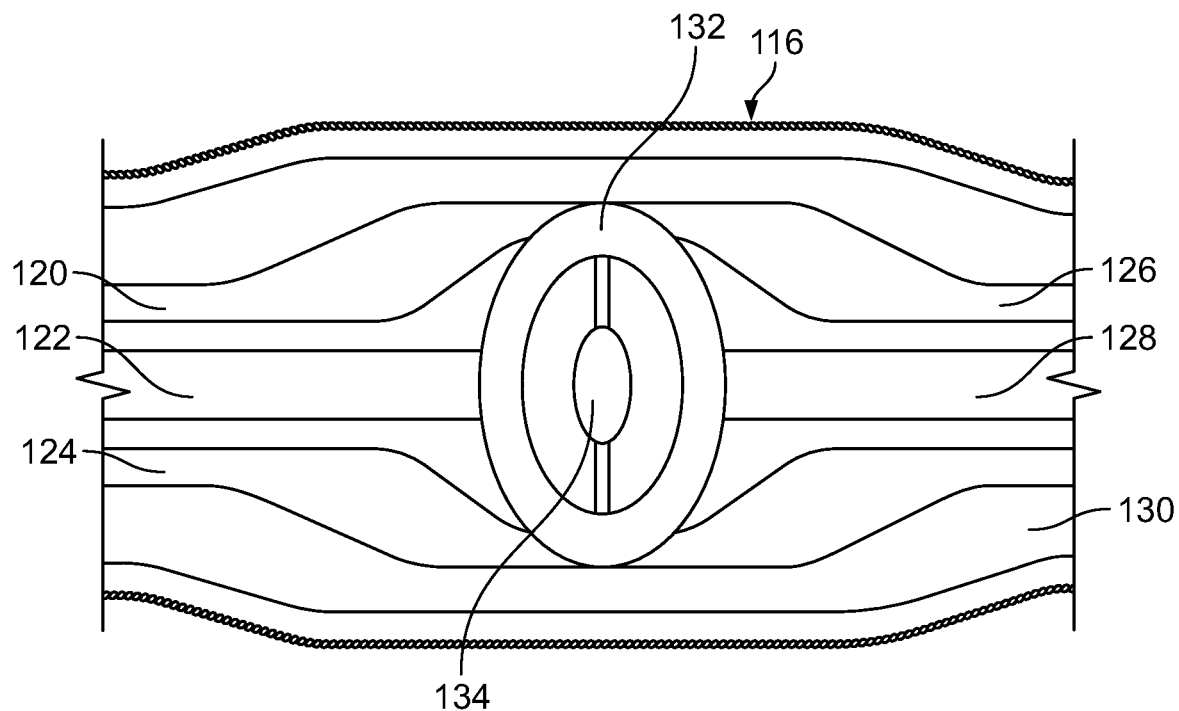
FIGS. 6A-B are perspective front and back views of a wider front torso portion of a hernia belt according to another embodiment.
Figure 6B:
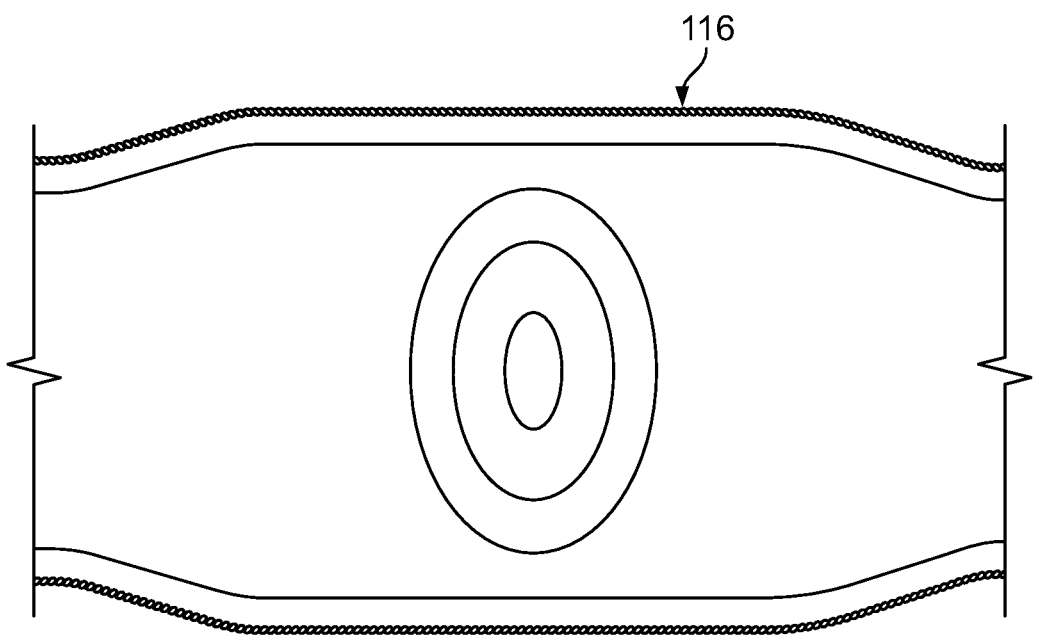

A. Stitch:1 Needle Cast-On Start
   Yarn: 2 Ends Polyamide+1 End Spandex
B. Stitch: 3 rows Double Jersey
   Yarn: 2 Ends Polyamide+1 End Spandex
C. Stitch: 4 rows Double Jersey Stitches+4 rows HORIZONTAL Inlay elastic sandwiched between Double Jersey layers
   Yarn: 4 Ends Polyamide+2 Ends Spandex+1 End Inlay Spandex
D. Stitch: 17-21 rows Double Jersey Stitches+HORIZONTAL Inlay Spandex yarn sandwiched between Double Jersey layers
   Yarn: 4 Ends Polyamide+2 Ends Spandex+1 End Inlay Spandex
E. Pattern Repeat Stitch: 6 rows: Float HORIZONTAL Inlay Spandex 2 needles to the FRONT exterior layer+alternating 2 needle Light Grey Double Jersey yarn coming to the FRONT. Inlay yarn is sandwiched between front and back double jersey layers in a HORIZONTAL direction.
   Yarn: 4 Ends Polyamide (2 front+2 back)+2 Ends Spandex (1 front+1 back)+1End Alternating Inlay Spandex
F. Stitch: 8-12 rows Double Jersey Stitches+HORIZONTAL Inlay Spandex yarn sandwiched between Double Jersey layers.
   Yarn: 4 Ends Polyamide+2 Ends Spandex+1 End Inlay Spandex
G. Stitch: 1 row crotchet bind-off end
   Yarn: 2 Ends Polyamide+1 End Spandex FIGS. 6A and 6B show a wider front torso portion 116 of a hernia belt according to an embodiment. FIG. 6A is a front view (i.e. outer surface view) and FIG. 6B is a back view (i.e. body facing surface view) of the wider front torso portion 116. As shown, the wider front torso portion 116 comprises a pattern of mesh stitch layouts 120, 122, 124, 126, 128, 130, 132, 134 including an oval target mesh stitch layout 134 and an oval ring target mesh stitch layout 132 to assist a user in centering the wider front torso portion 116 over a stoma while providing breathability and compression for supporting a herniated peristomal area.

Figure 7A:
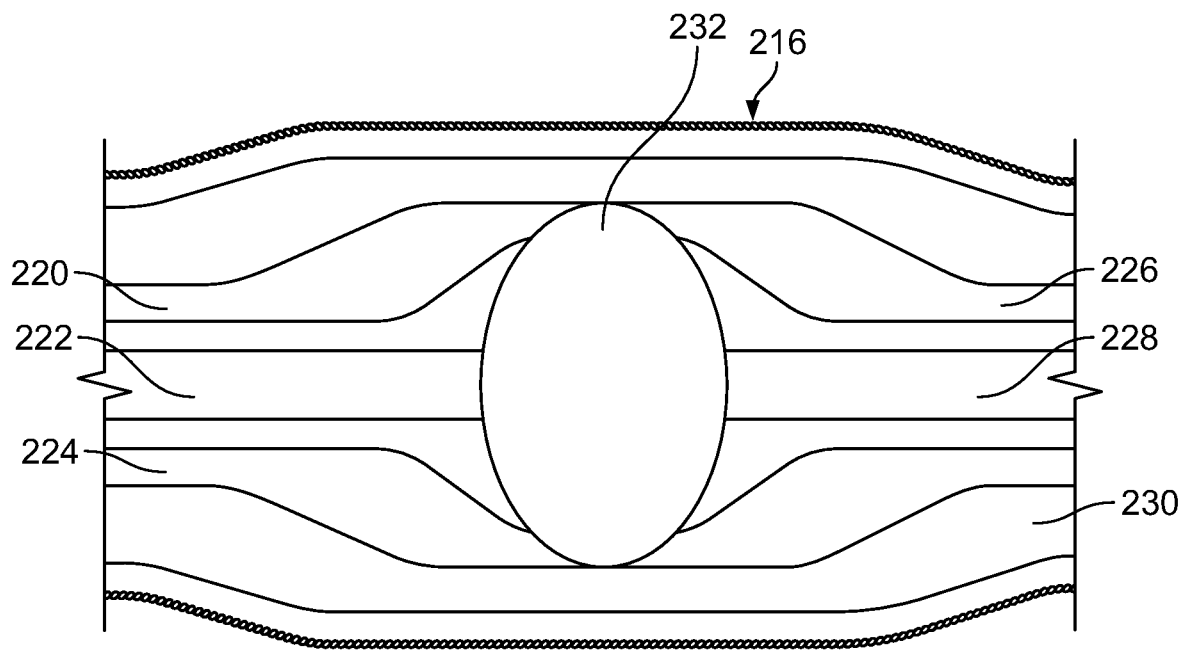
FIGS. 7A-B are perspective front and back views of a wider front torso portion of a hernia belt according to yet another embodiment.
Figure 7B:
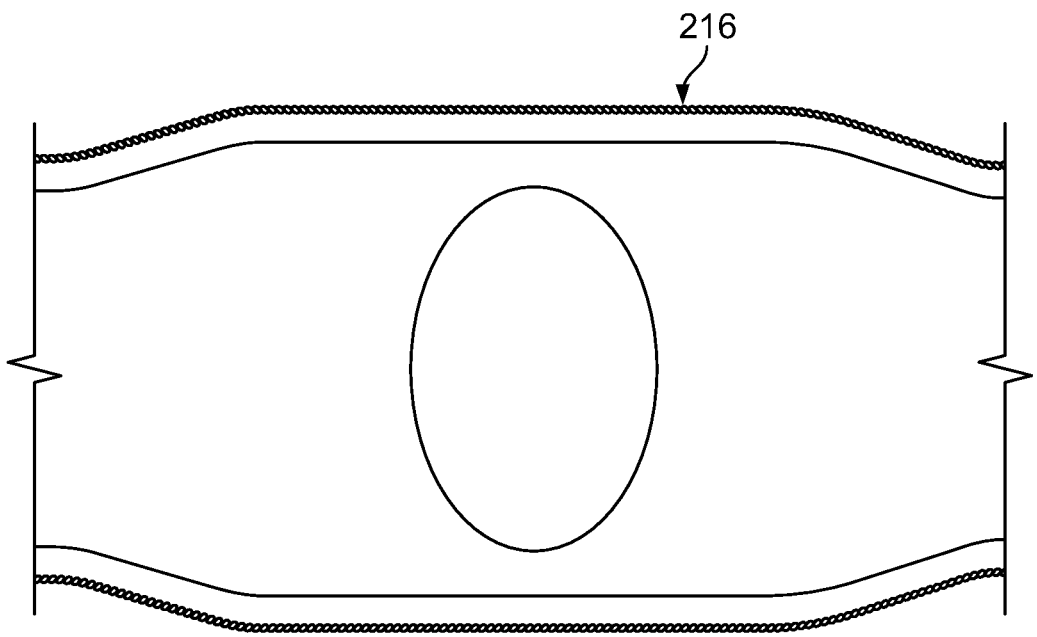

FIGS. 7A and 7B show a wider front torso portion 216 of a hernia belt according to another embodiment. FIG. 7A is a front view (i.e. outer surface view) and FIG. 7B is a back view (i.e. body facing surface view) of the wider front torso portion 216. As shown, the wider front torso portion 216 comprises a pattern of mesh stitch layouts 220, 222, 224, 226, 228, 230, 232 including an oval target mesh stitch layout 232 to assist a user in centering the wider front torso portion 216 over a stoma while providing breathability and compression for supporting a herniated peristomal area.

FIG. 8 shows a hernia belt 300 including a wider front torso portion 316 and a narrower portion 318 according to an embodiment. As shown, the wider front torso portion 316 comprises a pattern of mesh stitch layouts 320, 322 to assist a user in centering the wider front torso portion 316 over a stoma while providing breathability and compression for supporting a herniated peristomal area. FIG. 9 shows a hernia belt 400 including a wider front torso portion 416 and a narrower portion 418 according to yet another embodiment. As shown, the wider front torso portion 416 comprises a pattern of mesh stitch layouts 420, 422, 424 to assist a user in centering the wider front torso portion 416 over a stoma while providing breathability and compression for supporting a herniated peristomal area.

Referring now to FIGS. 10A-B, a hernia belt 500 according to yet another embodiment. Similar to the foregoing embodiments, the hernia belt 500 may generally include a support belt 502 formed as a one-piece knit construction and a two-part fastening system 504, 505. In this embodiment, the support belt 502 may be knitted to provide a generally rectangular shaped body having a tapered end portion 506 as shown in FIGS. 10A-B. The two-part fastening system may include a first part 504 and a second part 505 comprising a plurality of fasteners 508, 510, 512, 514, 516.

The support belt 502 may be knitted using a number of different yarns incorporating a plurality of stitch types. In an embodiment, the support belt 502 may be knitted using a digital knitting technology to provide a generally rectangular one-piece construction having a length $L_1$ and a width $W_1$, and a tapered end portion 506. The support belt 502 may be configured to have a generally constant width $W_1$ except in the tapered end portion 506, wherein the width gradually decreases for $W_1$ to $W_2$. Further, the support belt 506 may be knitted to provide rounded corners. The digital knitting of the support belt 502 may incorporate different stitch types, such as plated double jersey, faux mesh stitch, cast-on edge, bind-off edge, and birdseye jersey, using a number of different yarns to provide a desired shape and properties. For example, the support belt 502 may be configured to stretch about 10% to about 40% with force to stretch of about 0.2 kg per inch of the belt width per each 10% stretch of the belt length. The force to stretch is measured by placing a hernia belt flat on a long board with fasteners unattached, clamping one end of the hernia belt to the board, and stretching the other end of the hernia belt to record the force to stretch.

In an embodiment, the support belt 502 may comprise a plurality of mesh layouts 518, 520, 522, background areas 524, 526, 528, 530, and boundary areas 532. The background areas 524, 526, 528, 530 may be configured to provide sufficient compression to prevent a hernia or to support a herniated peristomal area. In an embodiment, the background areas 524, 526, 528, 530 may be knitted using a combination of soft polyamide yarns and stretchy yarns to provide an adequate knit tension for the required compression while providing desirable softness against skin and capability to wick sweat and moisture for improved user comfort.

As discussed above regarding the mesh stitch layouts in the foregoing embodiments, the mesh layouts 518, 520, 522 may be configured to provide breathable areas while providing sufficient compression to support a herniated peristomal area. In the embodiment of FIGS. 10A-B, the plurality of mesh layouts include first mesh layout 518, a second mesh layout 520, and a third mesh layout 522, each extending across the length $L_1$ of the support belt 502 generally parallel to each other. In other embodiments, the plurality of mesh layouts may include one or two or more than three mesh layouts. In the embodiment of FIGS. 10A-B, the plurality of mesh layouts 518, 520, 522 may be generally centered across the width $W_1$ and arranged between the background areas 524, 530, wherein the mesh layouts are separated from each other by the background areas 526, 528. Each of the mesh layouts 518, 520, 522 may include a plurality of wider portions 534 and a plurality of narrower portions 536. In an embodiment, the plurality of mesh layouts 518, 520, 522 may constitute about 20% to about 45% of the total area of the support belt 502, preferably about 25% to about 40%, and more preferably about 30% to about 35%.

The boundary areas 532 may be configured to frame the shape of the support belt 502 and to prevent curling of the hernia belt 500 while wearing and moving. In some embodiments, the boundary areas 532 may comprise a mesh area.

Figure 11A:
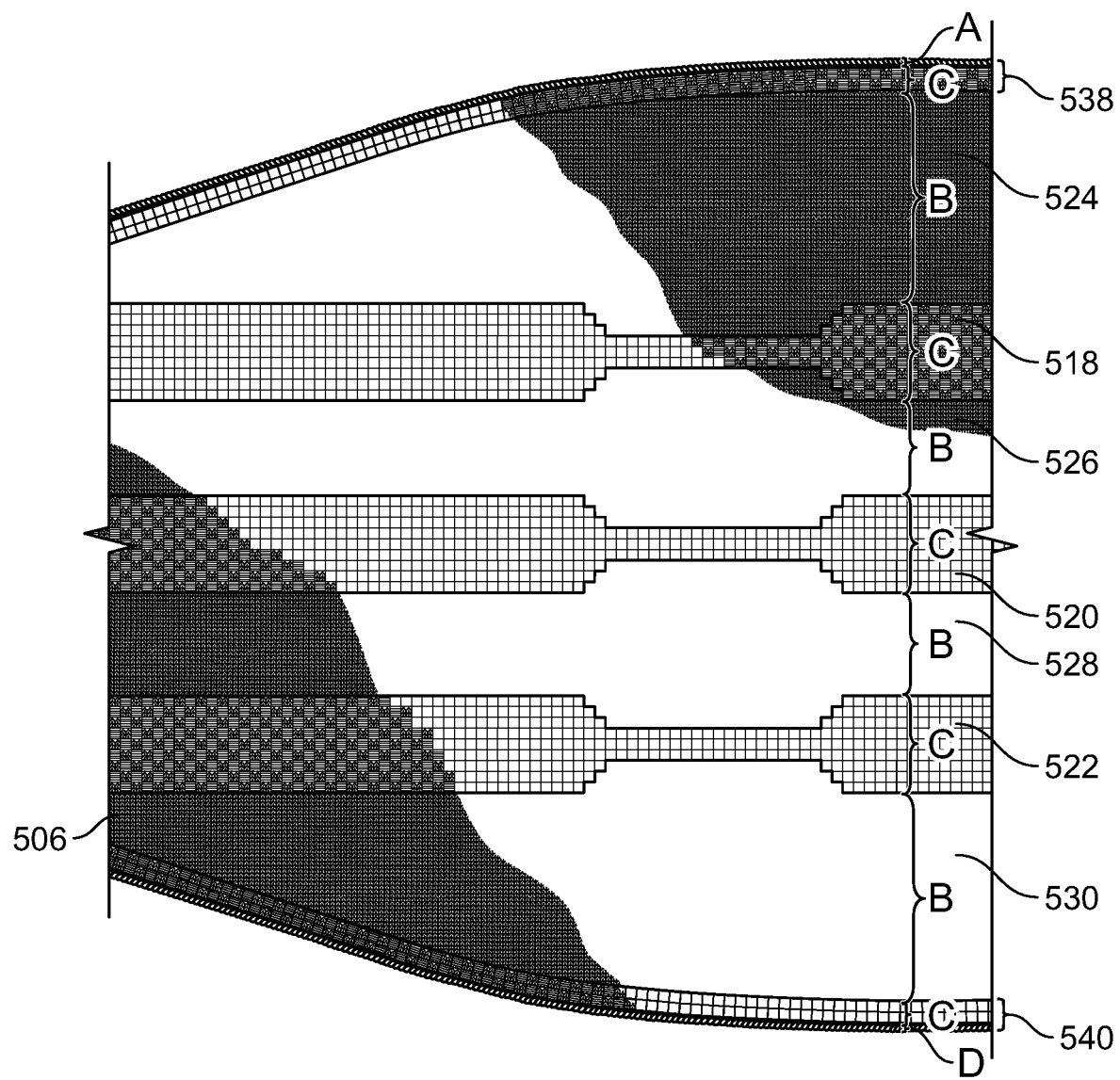
FIGS. 11A-B are enlarged front and back views of a portion of the hernia belt of FIGS. 10A-B.
Figure 11B:
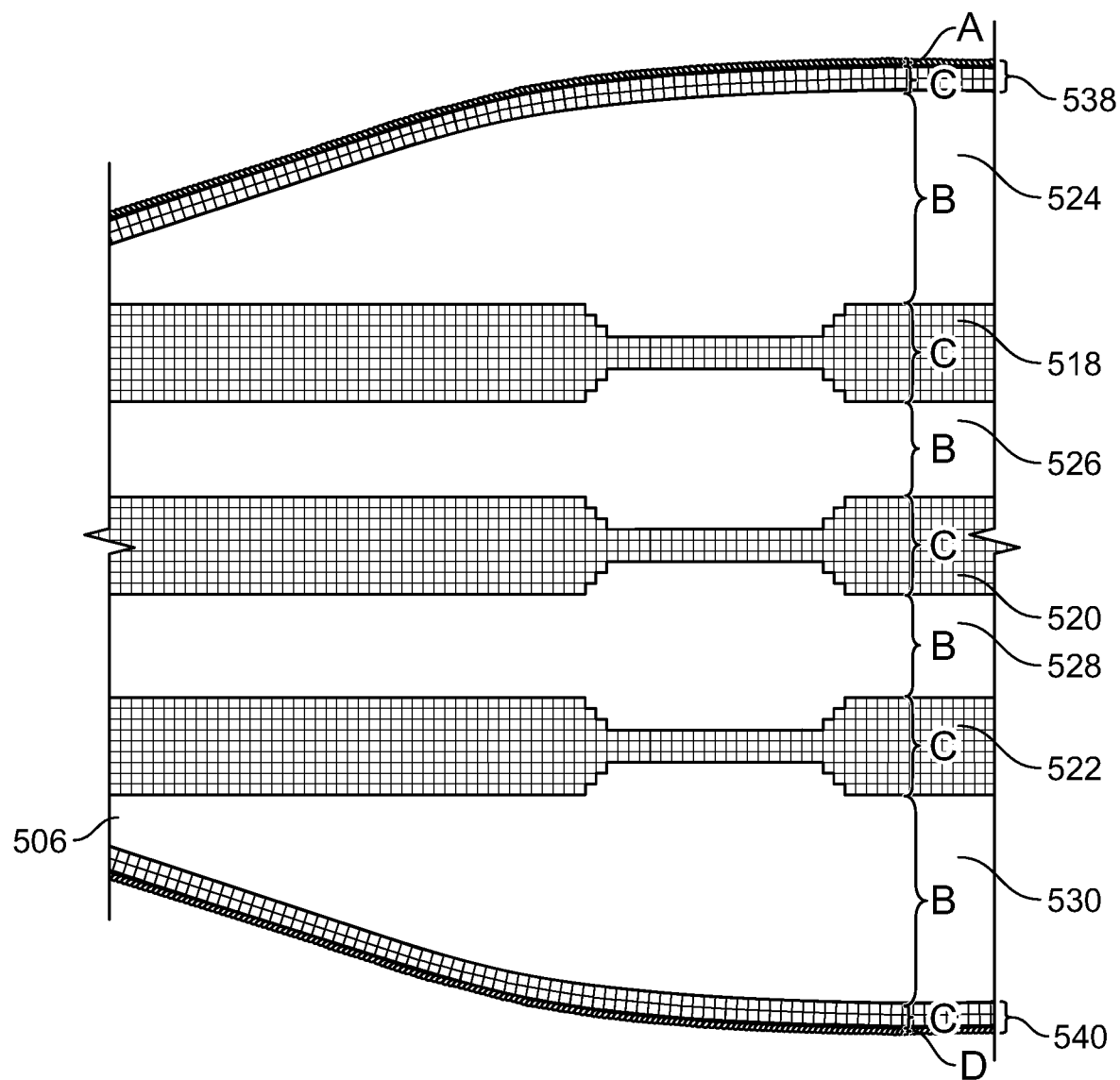

FIG. 11A illustrates an enlarged front view and FIG. 11B illustrates an enlarged back view of a portion of the support belt 502 proximate the tapered end portion 506. Table 1 provides stitch/yarn layouts of the support belt 502 according to an embodiment.

TABLE 1

| | Stitch/Yarn Layout | |
| --- | --- | --- |
| Area | Stitch | Yarns |
| Zone A | 1 Needle Cast-On Start | 4 Ends Polyamide + 2 Ends Spandex |
| Zone B | Double Jersey with Embedded Inlay | 4 Ends Polyamide (2 front + 2 back) 2 Ends Spandex (1 front + 1 back) 1End Embedded Inlay Spandex |
| Zone C | Double Jersey Stitches + Exposed Horizontal Inlay Spandex yarn sandwiched between Double Jersey layers | 4 Ends Polyamide (2 front + 2 back) 2 Ends Spandex (1 front + 1 back) 1End Alternating Inlay Spandex |
| Zone D | 1 Needle finishing Bind-Off Stitch, Horizontal direction | 4 Ends Polyamide (2 front + 2 back) 2 Ends Spandex (1 front + 1 back) |

The polyamide yarns used for knitting the support belt 502 may be formed from textured trilobal polyamide fibers and may have a yarn size of about 34/30/3 decitex (dtex) to about 80/70/3 dtex, and preferably about 78/46/3 dtex. In some embodiments, different color polyamide yarns, for example, light grey polyamide yarns and dark grey polyamide yarns, may be used for plating stitches. Further, the polyamide yarns may be configured to provide moisture wicking properties. In such an embodiment, the trilobal geometry and twists in polyamide yarn filaments may be configured to wick moisture and allow vapor to release from the support belt 502.

The spandex yarns may be formed from polyamide covered elastane fibers and may have a polyamide covering size of about 50/12/1 dtex to about 100/30/1 dtex, and preferably about 78/18/1 dtex with an elastane core size of about 90 dtex to about 250 dtex, and preferably about192 dtex. In an embodiment, the spandex yarn may comprise about 19% elastane and about 81% polyamide. The spandex yarns may be configured to provide desired softness of the support belt 502. A heavier elastic yarn, such as polyamide (PA 6.6) covered elastane (e.g. Lycra), may be used as the inlay spandex yarns. The inlay spandex yarns may have a polyamide covering size of about 60/20/2 dtex to about 85/40/2 dtex, preferably about 110/34/2 dtex and an elastane core size of about 800 dtex to about 1,500 dtex, and preferably about 1240 dtex. The inlay spandex yarns may be configured to provide desired stretch and recovery properties of the support belt 502.

Figure 12:
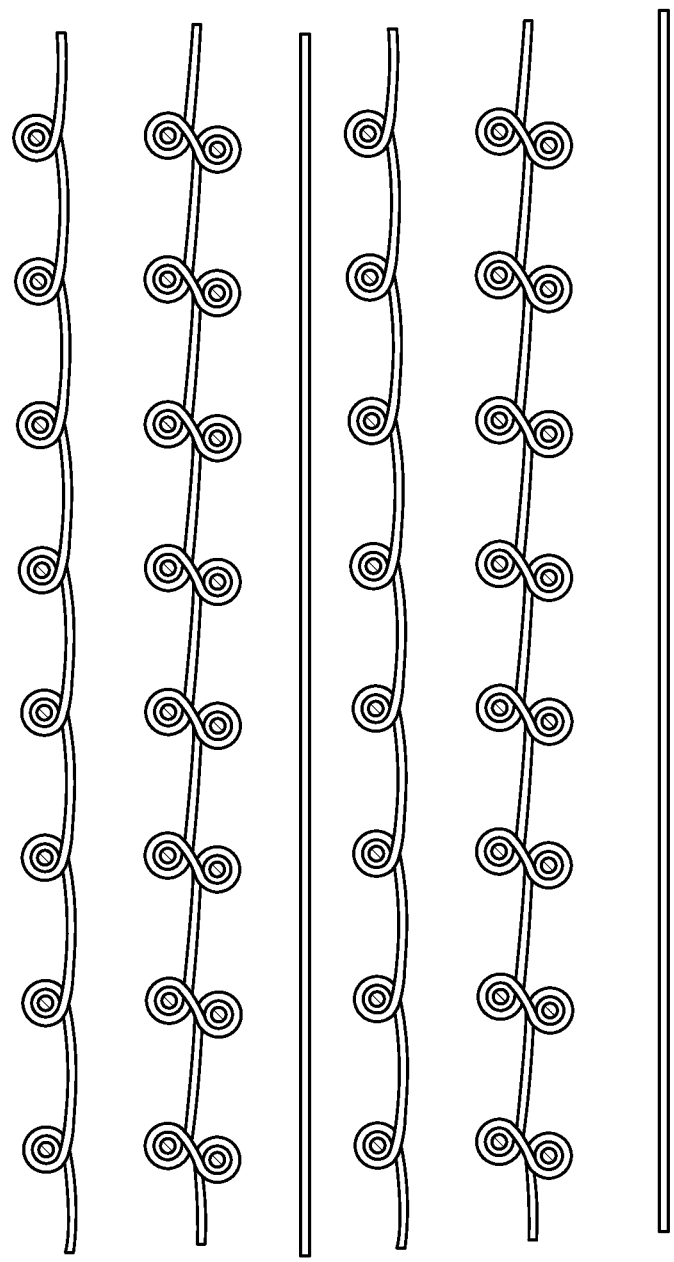
FIG. 12 is an illustration of a knitting notation for background areas of a hernia belt according an embodiment.

The background areas 524, 526, 528, 530 may be knitted using a plated double jersey knitting operation according to Zone B stitch/yarn layout provided in Table 1. In an embodiment, the background areas 524, 526, 528, 530 may be knitted using an Ikat marl plating technique with an elastic inlay yarn knitted between plating layers in a horizontal direction. The stitch/yarn layout of the background areas 524, 526, 528, 530 may be configured such that the hernia belt 500 may remain within about 75% to about 125% of its initial stretch and recovery values for a six-month use life. FIG. 12 illustrates a knitting notation for the Double Jersey stitches with Embedded Inlay according Zone B stitch/yarn layout.

Figure 13:
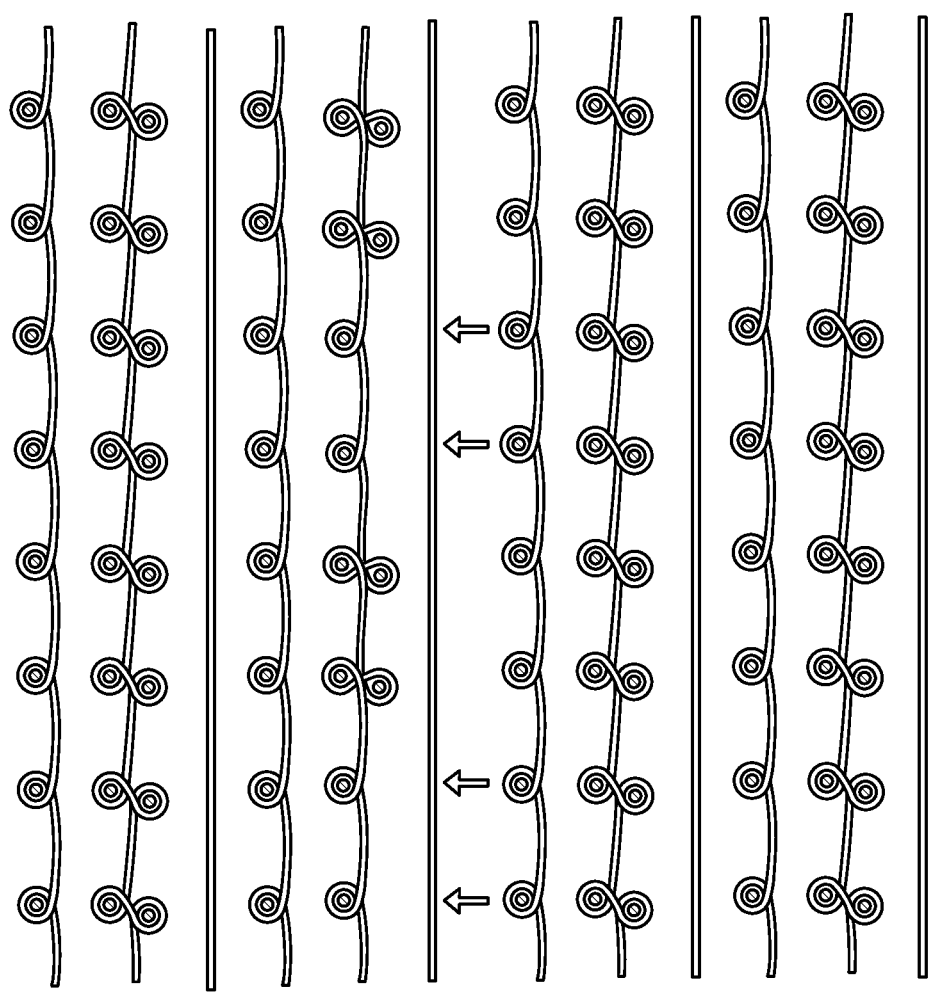
FIG. 13 is an illustration of a knitting notation for mesh layouts of a hernia belt according to an embodiment.

The plurality of mesh layouts 518, 520, 522 and mesh layouts in the boundary areas 532 may be knitted using a Faux Mesh stitch operation according to Zone C stitch/yarn layout to provide flexibility and breathability. FIG. 13 illustrates a knitting notation for the Faux Mesh stitches according to Zone C stitch/yarn layout.

The boundary areas 532 may comprise an upper boundary area 538, a lower boundary area 540, and side boundary areas 539, 541. In an embodiment, the upper boundary area 538 may comprise an outer Cast-On stitch layout according to Zone A stitch/yarn layout and an inner mesh layout according to Zone C stitch/yarn layout. The lower boundary area 540 may comprise an outer Bind-Off stitch layout according to Zone D stitch/yarn layout and an inner mesh layout according to Zone C stitch/yarn layout. The outer Cast-On stitch layout may be knitted using a Cast-On self edge-fully fashioning operation to start the knitting process and to provide a clean edge for the support belt 502. The outer Bind-Off stitch layout may be knitted using a Bind-Off self edge-fully fashioning operation to finish the knitting process and to provide a clean edge. The start and finish knitting operations may be configured to provide rounded corners. The side boundary areas 539, 541 may be knitted using a Birdseye Jersey Roll self edge operation to provide a curl around the edges of the side boundary areas 539, 541 and to conceal any inlay looping.

The two-part fastening system may include a first part 504 and a second part 505 comprising a plurality of fasteners 508, 510, 512, 514, 516 for securing the hernia belt 500 around a user's abdomen. In an embodiment, the first part 504 may be arranged in the tapered end portion 506 on a back side surface of the hernia belt 500 as shown in FIG. 10B, while the second part 505 comprising the plurality of fasteners 508, 510, 512, 514, 516 may be arranged proximate the opposite end on a front side surface as shown in FIG. 10A. In the embodiment of FIG. 10A, the plurality of fasteners 508, 510, 512, 514, 516 may be arranged in an area within the boundary areas 532 having a width $W_3$ and a length $L_2$. The fasteners 508, 510, 512, 514, 516 may be arranged spaced apart from each other with a gap 542, 544, 546, 548 therebetween. The spaced arrangement of the fasteners 508, 510, 512, 514, 516 may provide an extended fastener area while still allowing the underlying support belt 502 to stretch between fasteners. The extended fastener area may allow greater size adjustments for the hernia belt 500.

In an embodiment, a first fastener 508 and a last fastener 516 may be configured to have a generally triangular body having an angle $\theta_1$ of about 60°. In some embodiments, the last fastener 516 may be provided with a rounded corner as shown in FIGS. 10A-B. Second, third, and fourth fasteners 510, 512, 514 may be configured to have a generally parallelogram body having an angle $\theta_2$ of about 60° as shown in FIG. 10A. The plurality of fasteners 508, 510, 512, 514, 516 may be arranged to spread over an area having a width $W_3$ and a length L2, and separated from each other with gaps 542, 544, 546, 548 allowing the support belt 502 to stretch between the fasteners.

Figure 14A:
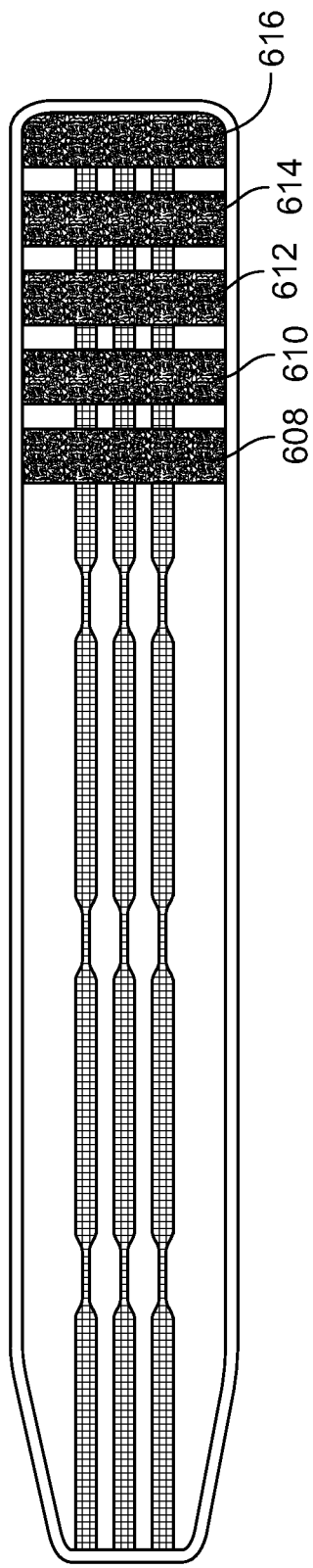
FIG. 14A-B are perspective front and back views of a hernia belt according to an embodiment.
Figure 14B:
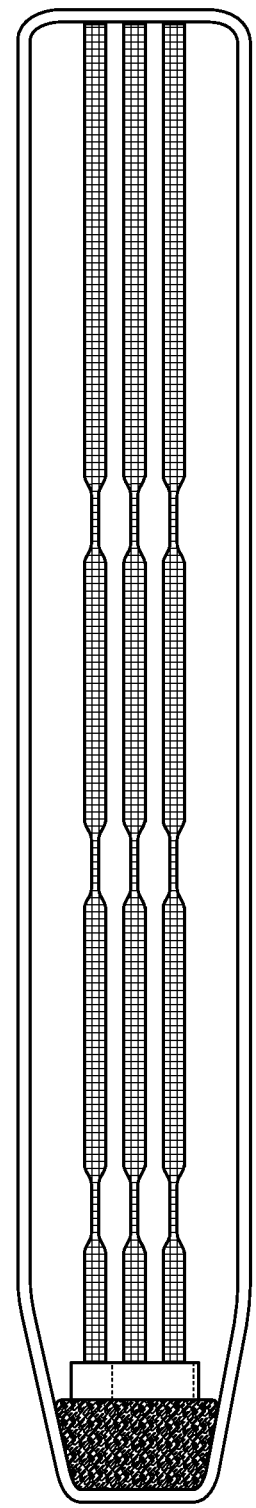
Figure 16A:
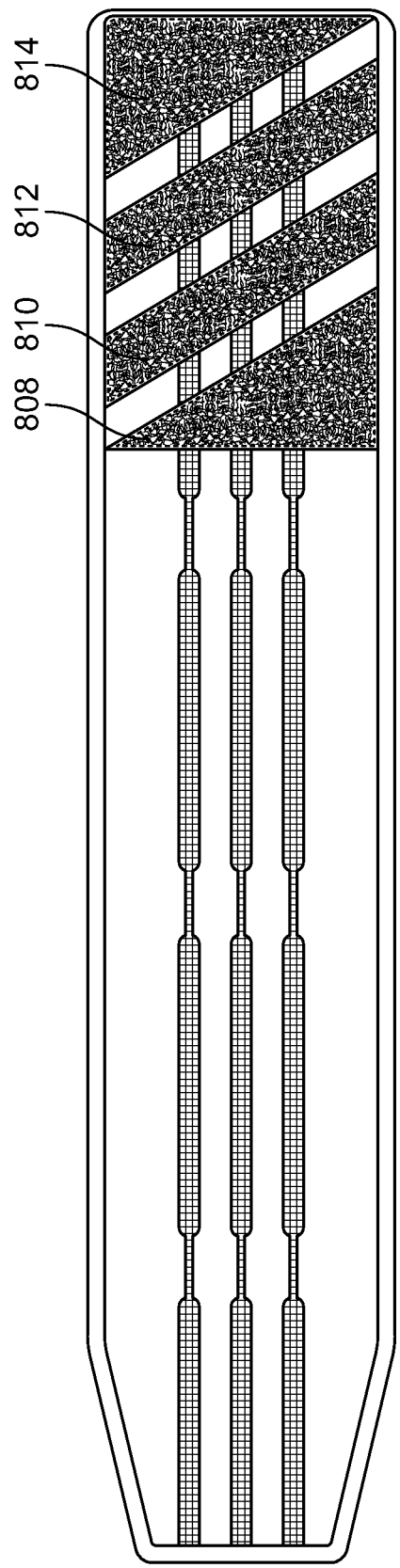
FIG. 16A-B are perspective front and back views of a hernia belt according to yet another embodiment.
Figure 16B:
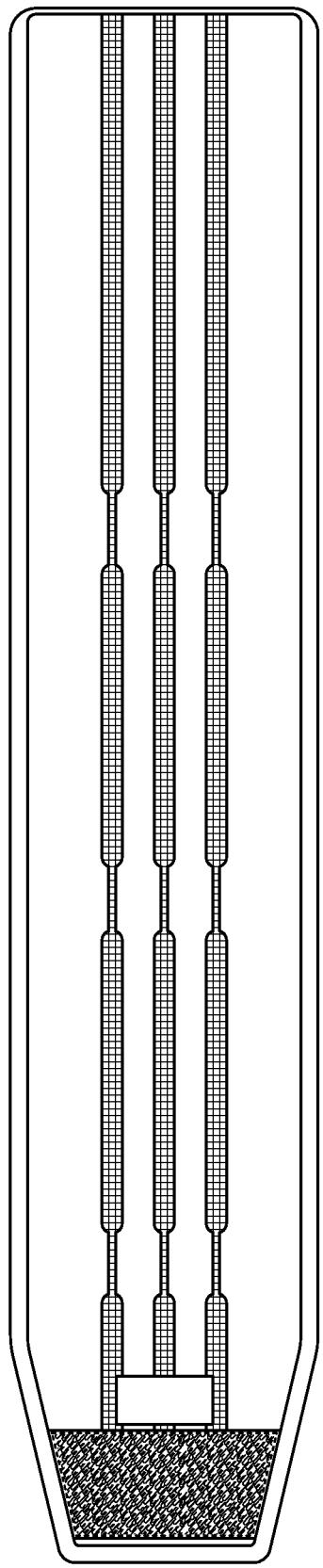

In other embodiments, the plurality of fasteners may include less than five fasteners or more than five fasteners, each of which is separated from an adjacent fastener by a gap. For example, the plurality of fasteners may include three fastener strips 708, 710, 712 as shown in FIG. 15A or four fastener strips 808, 810, 812, 814 as shown in 16A. The fasteners may be arranged diagonally as shown in FIGS. 10A, 15A, 16A. In another embodiment, the plurality of fasteners may be arranged vertically and include fastener strips 608, 610, 612, 614, 616 having a generally rectangular body separated from each other by a generally rectangular gap as shown in FIG. 14A. In yet another embodiment, the plurality of fasteners may include curved strips, and arranged spaced apart from each other accordingly to allow the underlying support belt to stretch between the curved strips.

In an embodiment, the two-part fastening system may comprise hook and loop fasteners as marketed under the Velcro trademark. Alternatively, the first and second fasteners may comprise a polypropylene material of the type sold under the trademark DUOTEC by G. Binder GmbH & Co. Holzgerlingen, Germany, which is stated in product literature to work on the principle of interlocking mushroom elements, which are designed so both fasteners can be identical.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A hernia belt, comprising:
   a support belt formed from a stretchable material and including a first peripheral end and a second peripheral end; and
   a two-part fastening system configured to secure the hernia belt on a user's body, wherein the two-part fastening system includes a first part arranged on the support belt proximate the first peripheral end and a second part comprising a plurality of fasteners arranged spaced apart from each other on the support belt proximate the second peripheral end,
   wherein the first part comprises a single fastener attached to a back side surface of the support belt, wherein the plurality of fasteners are attached to a front side surface of the support belt, wherein the plurality of fasteners include a first fastener, a second fastener, a third fastener, a fourth fastener, and a fifth fastener, wherein the second, third, fourth fasteners are arranged between the first and fifth fasteners with the fifth fastener arranged proximate the second peripheral end of the support belt, wherein each of the first and fifth fasteners has a generally triangular shaped body and each of the second, third, and fourth fasteners has a generally parallelogram shaped body, wherein the first fastener is arranged adjacent the second fastener with a gap therebetween, and the third fastener is arranged adjacent the second fastener with a gap therebetween, and the fourth fastener is arranged adjacent the third fastener with a gap therebetween, and the fifth fastener is arranged adjacent the fourth fastener with a gap therebetween, wherein the plurality of fasteners are arranged diagonally.

2. The hernia belt of claim 1, wherein the support belt is formed from a one-piece knit construction and comprises background areas, mesh layouts, and boundary areas, wherein the mesh layouts are configured to provide larger gaps between stitches than the background areas when stretched to provide breathable areas.

3. The hernia belt of claim 1, wherein the support belt has a generally rectangular shaped body including a tapered portion proximate the first peripheral end, wherein the corners of the support belt are rounded.

* * * * *